United States Patent [19]

Axen

[11] 4,410,695

[45] Oct. 18, 1983

[54] 2-DECARBOXY-2-TETRAZOLYL-6-KETO-PG COMPOUNDS

[75] Inventor: Udo F. Axen, Plainwell, Mich.

[73] Assignee: The Upjohn Company, Kalamazoo, Mich.

[21] Appl. No.: 85,834

[22] Filed: Oct. 17, 1979

Related U.S. Application Data

[60] Division of Ser. No. 959,400, Nov. 9, 1978, Pat. No. 4,215,222, which is a division of Ser. No. 819,857, Jul. 28, 1977, Pat. No. 4,158,667, which is a continuation-in-part of Ser. No. 725,548, Sep. 22, 1976, abandoned, which is a continuation-in-part of Ser. No. 716,972, Aug. 23, 1976, abandoned, which is a continuation-in-part of Ser. No. 655,110, Feb. 4, 1976, abandoned.

[51] Int. Cl.³ ............... C07D 257/04; A61K 31/41
[52] U.S. Cl. ............................ 542/426; 548/253; 424/269; 542/429
[58] Field of Search ............... 548/253; 542/426, 429

[56] References Cited

U.S. PATENT DOCUMENTS

| | | | |
|---|---|---|---|
| 3,883,513 | 5/1975 | Hess et al. | 424/269 |
| 4,124,601 | 11/1978 | Smith | 542/426 |
| 4,150,667 | 6/1979 | Axen | 260/413 |
| 4,210,748 | 7/1980 | Johnson | 542/426 |
| 4,223,157 | 9/1980 | Axen | 560/53 |
| 4,235,998 | 11/1980 | Johnson | 542/42 |
| 4,236,025 | 11/1980 | Axen | 560/255 |
| 4,262,118 | 4/1981 | Sih | 542/429 |

*Primary Examiner*—Mark L. Berch
*Assistant Examiner*—D. B. Springer
*Attorney, Agent, or Firm*—L. Ruth Hattan

[57] ABSTRACT

The present invention relates to novel 2-decarboxy-2-tetrazolyl-6-keto-PG compounds, which are useful for inducing a variety of prostacyclin-like pharmacological effects. Accordingly, these compounds are useful pharmacological agents for the same purposes for which prostacyclin is employed.

1 Claim, No Drawings

2-DECARBOXY-2-TETRAZOLYL-6-KETO-PG COMPOUNDS

CROSS REFERENCE TO RELATED APPLICATION

The present application is a divisional application of copending application Ser. No. 959,400, filed Nov. 9, 1978; now U.S. Pat. No. 4,215,222 which is a divisional application of Ser. No. 819,857, filed July 28, 1977, now U.S. Pat. No. 4,158,667; which is a continuation-in-part of Ser. No. 725,548, filed Sept. 22, 1976, now abandoned; which is a continuation-in-part of Ser. No. 716,972, filed Aug. 23, 1976, now abandoned; which is a continuation-in-part of Ser. No. 655,110, filed Feb. 4, 1976, now abandoned.

BACKGROUND OF THE INVENTION

The present invention relates to novel 2-decarboxy-2-tetrazolyl-6-keto-PG compounds, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention are incorporated here by reference from U.S. Pat. No. 4,158,667.

SUMMARY OF THE INVENTION

The present invention particularly provides:
A compound of the formula

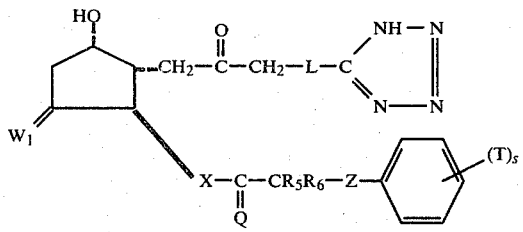

wherein
$W_1$ is $\alpha$—OH:$\beta$—H, $\alpha$—H:$\beta$—OH, oxo, methylene, $\alpha$—H:⊖—H, $\alpha$—CH$_2$OH:$\beta$—H;
wherein L is
(1) —(CH$_2$)$_d$—C(R$_2$)$_2$,
(2) —CH$_2$—O—CH$_2$—Y—, or
(3) —CH$_2$CH=CH—,
wherein d is zero to 5, $R_2$ is hydrogen, methyl, or fluoro, being the same or different with the proviso that one $R_2$ is not methyl when the other is fluoro, and wherein Y is a valence bond, —CH$_2$— or —(CH$_2$)$_2$,
wherein Q is keto, $\alpha$—H:$\beta$—H, $\alpha$—OH:$\beta$—R$_8$ or $\alpha$—R$_8$:$\beta$—OH
wherein R$_8$ is hydrogen or alkyl of one to 4 carbon atoms, inclusive;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (L13 O—) or C$_j$H$_{2j}$, wherein C$_j$H$_{2j}$ is a valence bond or alkylene of one to 9 carbon atoms, inclusive, with one to 6 carbon atoms, inclusive between CR$_5$R$_6$— and the phenyl ring;
wherein T is alkyl of one to 4 carbon atoms, inclusive, fluoro, chloro, trifluoromethyl, or —OR$_7$—, wherein R$_7$ is alkyl of one to 4 carbon atoms, inclusive, and s is zero, one, 2, or 3, with the proviso that not more than two T's are other than alkyl and when s is 2 or 3 the T's are either the same or different; and
wherein X is
(1) trans—CH=CH—,
(2) c is —CH=CH—,
(3) —C≡C—, or
(4) —CH$_2$CH$_2$—;
including the lower alkanoates thereof.

With regard to the divalent substituents described in the claims, e.g., Q and W$_1$, these divalent radicals are defined as $\alpha$—R$_i$:$\beta$—R$_j$, where R$_i$ represents a substituent of the divalent moiety of the alpha configuration with respect to the cyclopentane and R$_j$ represents a substituent of the divalent moiety of the beta configuration with respect to the cyclopentane ring. Accordingly, when Q is defined as $\alpha$—OH:$\beta$—R$_8$, the hydroxy of the Q moiety is in the alpha configuration, i.e., as in prostacyclin, and the R$_8$ substituent is in the beta configuration. Not all carbon atoms to which such divalent moieties are attached to represent asymmetric centers. For example, when both valence bonds are to hydrogen (e.g., W$_1$ or Q is $\alpha$—H:$\beta$—H), then no asymmetric center is present.

DESCRIPTION OF THE PREFERRED EMBODIMENTS

The present invention particularly relates to the following chemical compounds:
2-Decarboxy-2-tetrazolyl-6-keto-11$\beta$16-phenoxy-17,18,19,20-tetranor-PGF$_{1\alpha}$;
2-Decarboxy-2-tetrazolyl-6-keto-11-deoxy-16-phenoxy-17,18,19,20-tetranor-PGF$_{1\alpha}$;
2-Decarboxy-2-tetrazolyl-6-keto-13,14-didehydro-15(S)-16 phenoxy-17,18,19,20-tetranor-PGF$_{1\alpha}$;
2-Decarboxy-2-tetrazolyl-6-keto-13,14-didehydro-(15R)-16 -phenoxy-17,18,19,20-tetranor-PGF$_{1\alpha}$;
2-Decarboxy-2-tetrazolyl-6-keto-13,14-dihydro-16-phenoxy-17,18,19,20-tetranor-PGF$_{1\alpha}$;
2-Decarboxy-2-tetrazolyl-6,15-diketo-13,14-dihydro-16-phenoxy-17,18,19,20-tetranor-PGF$_{1\alpha}$;
2-Decarboxy-2-tetrazolyl-6-keto-16-phenoxy-17,18,19,20-tetranor-PGF$_{1\alpha}$;
2-Decarboxy-2-tetrazolyl-6-keto-16-phenoxy-17,18,19,20-tetranor-PGF$_{1\alpha}$, 11,15-diacetate;
2-Decarboxy-2-tetrazolyl-6,15-diketo-16-phenoxy-17,18,19,20-tetranor-PGF$_{1\alpha}$;
2-Decarboxy-2-tetrazolyl-6-keto-17-phenyl-18,19,20-trinor-PGF$_{1\alpha}$;
2-Decarboxy-2-tetrazolyl-6-keto-17-phenyl-18,19,20-trinor-13,14-dihydro-PGF$_{1\alpha}$;
2-Decarboxy-2-tetrazolyl-6-keto-17-phenyl-18,19,20-trinor-13,14-didehydro-PGF$_{1\alpha}$;
2-Decarboxy-2-tetrazolyl-6-keto-17-phenyl-18,19,20-trinor-cis-13-PGF$_{1\alpha}$;
2-Decarboxy-2-tetrazolyl-6-keto-17-m-trifluoromethylphenyl)-18,19,20-trinor-PGF$_{1\alpha}$;
2-Decarboxy-2-tetrazolyl-6-keto-17-m-chlorophenyl)-18,19,20-trinor-PGF$_{1\alpha}$;
2-Decarboxy-2-tetrazolyl-6-keto-17-(p-fluorophenyl)-18,19,20-trinor-PGF$_{1\alpha}$;
2-Decarboxy-2-tetrazolyl-6-keto-16,16-dimethyl-17-phenyl-18,19,20-trinor-PGF$_{1\alpha}$;

2-Decarboxy-2-tetrazolyl-6-keto-16,16-difluoro-17-phenyl-18,19,20-trinor-PGF$_{1\alpha}$;
2-Decarboxy-2-tetrazolyl-6-keto-16-(m-trifluoromethylphenoxy)-17,18,19,20-tetranor-PGF$_{1\alpha}$;
2-Decarboxy-2-tetrazolyl-6-keto-16-(m-chlorophenoxy)-17,18,19,20-tetranor-PGF$_{1\alpha}$;
2-Decarboxy-2-tetrazolyl-6-keto-16-(p-fluorophenoxy)-17,18,19,20-tetranor-PGF$_{1\alpha}$;
2-Decarboxy-2-tetrazolyl-6-keto-16-(methyl-16-phenoxy-18,19,20-trinor-PGF$_{1\alpha}$;
2-Decarboxy-2-tetrazolyl-6-keto-17-(m-trifluoromethylphenyl)-18,19,20-trinor-13,14-didehydro-PGF$_{1\alpha}$;
2-Decarboxy-2-tetrazolyl-6-keto-16-(m-chlorophenoxy)-17,18,19,20-tetranor-PGF$_{1\alpha}$;
2-Decarboxy-2-tetrazolyl-6-keto-16-(p-fluorophenoxy)-17,18,19,20-tetranor-PGF$_{1\alpha}$;
2-Decarboxy-2-tetrazolyl-6-keto-16-methyl-16-phenoxy-18,19,20-trinor-PGF$_{1\alpha}$;
2-Decarboxy-2-tetrazolyl-6-keto-17-(m-trifluoromethylphenyl)-18,19,20-trinor-13,14-didehydro-PGF$_{1\alpha}$;
2-Decarboxy-2-tetrazolyl-6-keto-17-(m-chlorophenyl)-18,19,20-trinor-13,14-didehydro-PGF$_{1\alpha}$;
2-Decarboxy-2-tetrazolyl-6-keto-17-(m-fluorophenyl)-18,19,20-trinor-13,14-didehydro-PGF$_{1\alpha}$;
2-Decarboxy-2-tetrazolyl-6-keto-16,16-dimethyl-17-phenyl-18,19,20-trinor-13,14-didehydro-PGF$_{1\alpha}$;
2-Decarboxy-2-tetrazolyl-6-keto-16,16-difluoro-17-phenyl-18,19,20-trinor-13,14-didehydro-PGF$_{1\alpha}$;
2-Decarboxy-2-tetrazolyl-6-keto-16-(m-trifluoromethylphenoxy)-17,18,19,20-tetranor-13,14-didehydro-PGF$_{1\alpha}$;
2-Decarboxy-2-tetrazolyl-6-keto-16-(m-chlorophenoxy)-17,18,19,20-tetranor-13,14,didehydro-PGF$_{1\alpha}$;
2-Decarboxy-2-tetrazolyl-6-keto-16-methyl-16-phenoxy-18,19,20-trinor-13,14-didehydro-PGF$_{1\alpha}$;
2-Decarboxy-2-tetrazolyl-6-keto-17-(m-trifluoromethylphenyl)-18,19,20-trinor-13,14-dihydro-PGF$_{1\alpha}$;
2-Decarboxy-2-tetrazolyl-6-keto-17-(m-chlorophenyl)-18,19,20-trinor-13,14-dihydro-PGF$_{1\alpha}$;
2-Decarboxy-2-tetrazolyl-6-keto-17-(m-fluorophenyl)-18,19,20-trinor-13,14-dihydro-PGF$_{1\alpha}$;
2-Decarboxy-2-tetrazolyl-6-keto-16,16-dimethyl-17-phenyl-18,19,20-trinor-13,14-dihydro-PGF$_{1\alpha}$;
2-Decarboxy-2-tetrazolyl-6-keto-16,16-difluoro-17-phenyl-18,19,20-trinor-13,14-dihydro-PGF$_{1\alpha}$;
2-Decarboxy-2-tetrazolyl-6-keto-16-(m-trifluoromethylphenoxy)-17,18,19,20-tetranor-13,14-dihydro-PGF$_{1\alpha}$;
2-Decarboxy-2-tetrazolyl-6-keto-16-(m-chlorophenoxy)-17,18,19,20-tetranor-13,14-dihydro-PGF$_{1\alpha}$;
2-Decarboxy-2-tetrazolyl-6-keto-16-(p-fluorophenoxy)-17,18,19,20-tetranor-13,14-dihydro-PGF$_{1\alpha}$;
2-Decarboxy-2-tetrazolyl-6-keto-16-methyl-16-phenoxy-18,19,20-trinor-13,14-dihydro-PGF$_{1\alpha}$;
2-Decarboxy-2-tetrazolyl-6-keto-17-(m-trifluoromethylphenyl)-18,19,20-trinor-cis-13-PGF$_{1\alpha}$;
2-Decarboxy-2-tetrazolyl-6-keto-17-(m-chlorophenyl)-18,19,20-trinor-cis-13-PGF$_{1\alpha}$;
2-Decarboxy-2-tetrazolyl-6-keto-17-(p-fluorophenyl)-18,19,20-trinor-cis-13-PGF$_{1\alpha}$;
2-Decarboxy-2-tetrazolyl-6-keto-16,16-dimethyl-17-phenyl-18,19,20-trinor-cis-13-PGF$_{1\alpha}$;
2-Decarboxy-2-tetrazolyl-6-keto-16,16-difluoro-17-phenyl-18,19,20-trinor-cis-13-PGF$_{1\alpha}$;
2-Decarboxy-2-tetrazolyl-6-keto-16-(m-trifluoromethylphenoxy)-17,18,19,20-tetranor-cis-13-PGF$_{1\alpha}$;
2-Decarboxy-2-tetrazolyl-6-keto-16-(m-chlorophenoxy)-17,18,19,20-tetranor-cis-13-PGF$_{1\alpha}$;
2-Decarboxy-2-tetrazolyl-6-keto-16-(p-fluorophenoxy)-17,18,19,20-tetranor-cis-13-PGF$_{1\alpha}$;
2-Decarboxy-2-tetrazolyl-6-keto-16-methyl-16-phenoxy-18,19,20-trinor-cis-13-PGF$_{1\alpha}$;
2-Decarboxy-2-tetrazolyl-6-keto-2,2-difluoro-17-phenyl-18,19,20-trinor-PGF$_{1\alpha}$;
2-Decarboxy-2-tetrazolyl-6-keto-2,2-difluoro-17-(m-trifluoromethylphenyl)-18,19,20-trinor-PGF$_{1\alpha}$;
2-Decarboxy-2-tetrazolyl-6-keto-2,2-difluoro-17-(m-chlorophenyl)-18,19,20-trinor-PGF$_{1\alpha}$;
2-Decarboxy-2-tetrazolyl-6-keto-2,2-difluoro-17-(p-fluorophenyl)-18,19,20-trinor-PGF$_{1\alpha}$;
2-Decarboxy-2-tetrazolyl-6-keto-2,2-difluoro-16,16-dimethyl-17-phenyl-18,19,20-trinor-PGF$_{1\alpha}$;
2-Decarboxy-2-tetrazolyl-6-keto-2,2-difluoro-16,16-difluoro-17-phenyl-18,19,20-trinor-PGF$_{1\alpha}$;
2-Decarboxy-2-tetrazolyl-6-keto-2,2-difluoro-16-phenoxy-17,18,19,20-tetranor-PGF$_{1\alpha}$;
2-Decarboxy-2-tetrazolyl-6-keto-2,2-difluoro-16-(m-trifluoromethylphenoxy)-17,18,19,20-tetranor-PGF$_{1\alpha}$;
2-Decarboxy-2-tetrazolyl-6-Keto-2,2-difluoro-16-(M-chlorophenoxy)-17,18,19,20-tetranor-PGF$_{1\alpha}$;
2-Decarboxy-2-tetrazolyl-6-keto-2,2-difluoro-16-(p-fluorophenoxy)-17,18,19,20-tetranor-PGF$_{1\alpha}$;
2-Decarboxy-2-tetrazolyl-6-keto-2,2-difluoro-16-methyl-16-phenoxy-18,19,20-trinor-PGF$_{1\alpha}$;
2-Decarboxy-2-tetrazolyl-6-keto-2,2-difluoro-17-phenyl-18,19,20-trinor-13,14-didehydro-PGF$_{1\alpha}$;
2-Decarboxy-2-tetrazolyl-6-keto-2,2-difluoro-17-(m-trifluoromethylphenyl)-18,19,20-trinor-13,14-didehydro-PGF$_{1\alpha}$;
2-Decarboxy-2-tetrazolyl-6-keto-2,2-difluoro-17-(m-chlorophenyl)-18,19,20-trinor-13,14-didehydro-PGF$_{1\alpha}$;
2-Decarboxy-2-tetrazolyl-6-keto-2,2-difluoro-17-(p-fluorophenyl)-18,19,20-trinor-13,14-didehydro-PGF$_{1}$;
2-Decarboxy-2-tetrazolyl-6-keto-2,2-difluoro-16,16-dimethyl-17-phenyl-18,19,20-trinor-13,14-didehydro-PGF$_{1\alpha}$;
2-Decarboxy-2-tetrazolyl-6-keto-2,2,16,16-tetrafluoro-17-phenyl-18,19,20-trinor-13,14-didehydro-PGF$_{1\alpha}$;
2-Decarbocxy-2tetrazolyl-6-keto-2,2-difluoro-16-phenoxy-17,18,19,20-tetranor-13,14-didehydro-PGF$_{1\alpha}$;
2-Decarboxy-2-tetrazolyl-6-keto-2,2-difluoro-16-(m-trifluoromethylphenoxy)-17,18,19,20-tetranor-13,14-didehydro-PGF$_{1\alpha}$;
2-Decarboxy-2-tetrazolyl-6-keto-2,2-difluoro-16-(m-chlorophenoxy)-17,18,19,20-tetranor-13,14-didehydro-PGF$_{1\alpha}$;
2-Decarboxy-2-tetrazolyl-6-keto-2,2-difluoro-16-methyl-16-phenoxy-18,19,20-trinor-13,14-didehydro-PGF$_{1\alpha}$;
2-Decarboxy-2-tetrazolyl-6-keto,-2,2-difluoro-17-phenyl-18,19,20-trinor-13,14-dihydro-PGF$_{1\alpha}$;
2-Decarboxy-2-tetrazolyl-6-keto-2,2-difluoro-17-(m-trifluoromethylphenyl)-18,19,20-trinor-13,14-dihydro-PGF$_{1\alpha}$;
2-Decarboxy-2-tetrazolyl-6-keto-2,2-difluoro-17-(m-chloropheny)-18,19,20-trinor-13,14-dihydro-PGF$_{1\alpha}$;
2-Decarboxy-2-tetrazolyl-6-keto-2,2-difluoro-17-(p-fluorophenyl)-18,19,20-trinor-13,14-dihydro-PGF$_{1\alpha}$;
2-Decarboxy-2-tetrazolyl-6-keto-2,2-difluoro-16,16-dimethyl-17-phenyl-18,19,20trinor-13,14-dihydro-PGF$_{1\alpha}$;
2-Decarboxy-2-tetrazolyl-6-keto-2,2,16,16-tetrafluoro-17phenyl-18,19,20-trinor-13,14-dihydro-PGF$_{1\alpha}$;

2-Decarboxy-2-tetrazolyl-6-keto-2,2-difluoro-16-phenoxy-17,18,19,20-tetranor-13,14-dihydro-PGF$_{1\alpha}$;
2-Decarboxy-2-tetrazolyl-6-keto-2,2-difluoro-16-(m-trifluoromethylohenoxy)-17,18,19,20-tetranor-13,14-dihydro-PGF$_{1\alpha}$;
2-Decarboxy-2-tetrazolyl-6-keto-2,2-difluoro-16-(m-chlorophenoxy)-17,18,19,20-tetranor-13,14-dihydro-PGF$_{1\alpha}$;
2-Decarboxy-2-tetrazolyl-6-keto-2,2-difluoro-16-(p-fluorophenoxy)-17,18,19,20-tetranor-13,14-dihydro-PGF$_{1\alpha}$;
2-Decarboxy-2-tetrazolyl-6-keto-2,2-difluoro-16-methyl-16-phenoxy-18,19,20-trinor-13,14-dihydro-PGF$_{1\alpha}$;
2-Decarboxy-2-tetrazolyl-6-keto-2,2-difluoro-17-phenyl-18,19,20-trinor-cis-13-PGF$_{1\alpha}$;
2-Decarboxy-2-tetrazolyl-6-keto-2,2-difluoro-17-(m-trifluoromethylphenyl)-18,19,20-trinor-cis-13-PGF$_{1\alpha}$;
2-Decarboxy-2-tetrazolyl-6-keto-2,2-difluoro-17-(m-chlorophenyl)-18,19,20-trinor-cis-13-PGF$_{1\alpha}$;
2-Decarboxy-2-tetrazolyl-6-keto-2,2-difluoro-17-(p-fluorophenyl)-18,19,20-trinor-cis-13-PGF$_{1\alpha}$;
2-Decarboxy-2-tetrazolyl-6-keto-2,2-difluoro-16,16-dimethyl-17-phenyl-18,19,20-trinor-cis-13-PGF$_{1\alpha}$;
2-Decarboxy-2-tetrazolyl-6-keto-2,2-difluoro-17-phenyl-18,19,20-trinor-cis-13-PGF$_{1\alpha}$;
2-Decarboxy-2-tetrazolyl-6-keto-2,2-diflouro-16-phenoxy-17,18,19,20-tetranor-cis-13-PGF$_{1\alpha}$;
2-Decarboxy-2-tetrazolyl-6-keto-2,2-difluoro-16-(m-trifluoromethylphenoxy)-17,18,19,20-tetranor-cis-13-PGF$_{1\alpha}$;
2-Decarboxy-2-tetrazolyl-6-keto-2,2-difluoro-16-(m-chlorophenoxy)-17,18,19,20-tetranor-cis-13PGF$_{1\alpha}$;
2-Decarboxy-2-tetrazolyl-6-keto-2,2-difluoro-16-(p-fluorophenoxyl)-17,18,19,20-tetranor-cis-13-PGF$_{1\alpha}$;
2-Decarboxy-2-tetrazolyl-6-keto-2,2-difluoro-16-methyl-16-phenoxy-18,19,20-trinor-cis-13-PGF$_{1\alpha}$;
2-Decarboxy-2-tetrazolyl-6-keto-3-oxa-17-phenyl-18,19,20-trinor-PGF$_{1\alpha}$;
2-Decarboxy-2-tetrazolyl-6-keto-3-oxa-17-(m-trifluoromethylphenyl)-18,19,20-trinor-PGF$_{1\alpha}$;
2-Decarboxy-2-tetrazolyl-6-keto-3-oxa-17-(m-chlorophenyl)-18,19,20-trinor,PGF$_{1\alpha}$;
2-Decarboxy-2-tetrazolyl-6-keto-3-oxa-16,16-dimethyl-17-phenyl-18,19,20-trinor-PGF$_{1\alpha}$;
2-Decarboxy-2-tetrazolyl-6-keto-3-oxa-16,16-difluoro-17-phenyl-18,19,20-trinor-PGF$_{1\alpha}$;
2-Decarboxy-2-tetrazolyl-6-keto-3-oxa-16-phenoxy-17,18,19,20-tetranor-PGF$_{1\alpha}$;
2-Decarboxy-2-tetrazolyl-6-keto-3-oxa-16-(m-trifluoromethylphenoxy)-17,18,19,20-tetranor-PGF$_{1\alpha}$;
2-Decarboxy-2-tetrazolyl-6-keto-3-oxa-16-(m-chlorophenoxy)-17,18,19,20-tetranor-PGF$_{1\alpha}$;
2;1-Decarboxy-2-tetrazolyl-6-keto-3-oxa-16-(p-fluorophenoxy)-17,18,19,20-tetranor-PGF$_{1\alpha}$;
2-Decarboxy-2-tetrazolyl-6-keto-3-oxa-16-methyl-16-phenoxy-18,19,20-trinor-PGF$_{1\alpha}$;
2-Decarboxy-2-tetrazolyl-6-keto-3-oxa-17-phenyl-18,19,20-trinor-13,14-didehydro-PGF$_{1\alpha}$;
2-Decarboxy-2-tetrazolyl-6-keto-3-oxa-17-(m-trifluoromethyplhenyl)-18,19,20-trinor-13,14-didehydro-PGF$_{1\alpha}$;
2-Decarboxy-2-tetrazolyl-6-keto-3-oxa-17-(m-chlorophenyl)-18,19,20-trinor-13,14-didehydro-PGF$_{1\alpha}$;
2-Decarboxy-2-tetrazolyl-6-keto-3-oxa-17-(p-fluorophenyl)-18,19,20-trinor,13,14-didehydro-PGF$_{1\alpha}$;
2-Decarboxy-2-tetrazolyl-6-keto-3-oxa-16,16-dimethyl-17-phenyl-18,19,20-trinor-13,14-didehydro-PGF$_{1\alpha}$;
2-Decarboxy-2-tetrazolyl-6-keto-3-oxa-16,16-difluoro-17-phenyl-18,19,20-trinor-13,14-didehydro-PGF$_{1\alpha}$;
2-Decarboxy-2-tetrazolyl-6-keto-3-oxa-16-phenoxy-17,18,19,20-tetranor-13,14-didehydro-PGF$_{1\alpha}$;
2-Decarboxy-2-tetrazolyl-6-keto-3-oxa-16-(m-trifluoromethylphenoxy)-17,18,19,20-tetranor-13,14-didehydro-PGF$_{1\alpha}$;
2-Decarboxy-2-tetrazolyl-6-keto-3-oxa-16-(m-chlorophenoxy)-17,18,19,20-tetranor-13,14-didehydro-PGF$_{1\alpha}$;
2-Decarboxy-2-tetrazolyl-6-keto-3-oxa-16-methyl-16-phenoxy-18,19,20-trinor-13,14-didehydro-PGF$_{1\alpha}$;
2-Decarboxy-2-tetrazolyl-6-keto-3-oxa-17-phenyl-18,19,20-trinor-13,14-dihydro-PGF$_{1\alpha}$;
2-Decarboxy-2-tetrazolyl- b 6-keto-3-oxa-17-(m-trifluoromethylphenyl)-18,19,20-trinor-13,14-dihydro-PGF$_{1\alpha}$;
2-Decarboxy-2-tetrazolyl-6-keto-3-oxa-17-(m-chlorophenyl)-18,19,20-trinor-13,14-dihydro-PGF$_{1\alpha}$;
2-Decarboxy-2-tetrazolyl-6-keto-3-oxa-17-(p-fluorophenyl)-18,19,20-trinor-13,14-dihydro-PGF$_{1\alpha}$;
2-Decarboxy-2-tetrazolyl-6-keto-3-oxa-16,16-dimethyl-17-phenyl-18,19,20-trinor-13,14-dihydro-PGF$_{1\alpha}$;
2-Decarboxy-2-tetrazolyl-6-keto-3-oxa-16,16-difluoro-17-phenyl-18,19,20-trinor-13,14-dihydro-PGF$_{1\alpha}$;
2-Decarboxy-2-tetrazolyl-6-keto-3-oxa-16-phenoxy-;b 17,18,19,20-tetranor-13,14-dihydro-PGF$_{1\alpha}$;
2-Decarboxy-2-tetrazolyl-6-keto-3-oxa-16-(m-trifluoromethylphenyl)-17,18,19,20-tetranor-13,14-dihydro-PGF$_{1\alpha}$;
2-Decarboxy-2-tetrazolyl-6-keto-3-oxa-16-(m-chlorophenoxy)-17,18,19,20-tetranor-13,14-dihydro-PGF$_{1\alpha}$;
2-Decarboxy-2-tetrazolyl-6-keto-3-oxa-16-(p-fluorophenoxy)-17,18,19,20-tetranor-13,14-dihydro-PGF$_{1\alpha}$;
2-Decarboxy-2-tetrazolyl-6-keto-3-oxa-16-methyl-16-phenoxy-18,19,20-trinor-13,14-dihydro-PGF$_{1\alpha}$;
2-Decarboxy-2-tetrazolyl-6-keto-3-oxa-17-phenyl-18,19,20-trinor-cis-13-PGF$_{1\alpha}$;
2-Decarboxy-2-tetrazolyl-6-keto-3-oxa-17-(m-trifluoromethylphenyl)-18,19,20-trinor-cis-13-PGF$_{1\alpha}$;
2-Decarboxy-2-tetrazolyl-6-keto-3-oxa-17-(m-chlorophenyl)-18,19,20-trinor-cis-13-PGF$_{1\alpha}$;
2-Decarboxy-2-tetrazolyl-6-keto-3-oxa-17-(p-fluorophenyl)-18,19,20-trinor-cis13-PGF$_{1\alpha}$;
2-Decarboxy-2-tetrazolyl-6-keto-3-oxa-16,16-dimethyl-17-phenyl-18,19,20-trinor-cis-13-PGF$_{1\alpha}$;
2-Decarboxy-2-tetrazolyl-6-keto-3-oxa-16,16-difluoro-17-phenyl-18,19,20-trinor-cis-13-PGF$_{1\alpha}$;
2-Decarboxy-2-tetrazolyl-6-keto-3-oxa-16-phenoxy-17,18,19,20-tetranor-cis-13-PGF$_{1\alpha}$;
2-Decarboxy-2-tetrazolyl-6-keto-3-oxa-16-(m-trifluoromethylphenoxy)-17,18,19,20-tetranor-cis-13-PGF$_{1\alpha}$;
2-Decarboxy-2-tetrazolyl-6-keto-3-oxa-16-(m-chlorophenoxy)-17,18,19,20-tetranor-cis-13-PGF$_{1\alpha}$;
2-Decarboxy-2-tetrazolyl-6-keto-3-oxa-(p-fluorophenoxy)-17,18,19,20-tetranor-cis-13-PGF$_{1\alpha}$;
2-Decarboxy-2-tetrazolyl-6-keto-3-oxa-16-methyl-16-phenoxy-18,19,20,-trinor-cis-13-PGF;hd 1$\alpha$; and
2-Decarboxy-2-tetrazolyl-6-keto-17-phenyl-18,19,20-trinor-PGF$_{1\alpha}$.

I claim:
1. A prostacyclin of formula

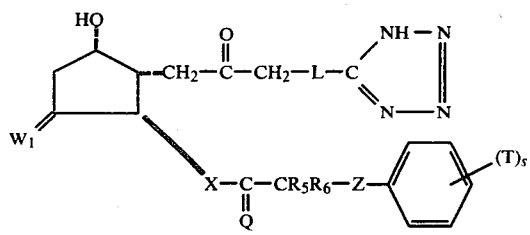

wherein $W_1$ is $\alpha$-OH:$\beta$-H, $\alpha$-H:$\beta$OH, oxo, methylene, $\alpha$-H:$\beta$-H, $\alpha$-CH$_2$OH:$\beta$-H;

wherein L is
(1) $-(CH_2)_d-C(R_2)_2$,
(2) $-CH_2-O-CH_2-Y-$, or
(3) $-CH_2CH=CH-$, wherein d is zero to 5, $R_2$ is hydrogen, methyl, or fluoro, being the same or different with the proviso that one $R_2$ is not methyl when the other is fluoro, and wherein Y is a valence bond, $-CH_2-$ or $-(CH_2)_2$, wherein Q is keto, $\alpha$-H:$\beta$-H, $\alpha$-OH:$\beta R_8$ or $\alpha$-$R_8$:$\beta$-OH wherein $R_8$ is hydrogen or alkyl of one to 4 carbon atoms, inclusive;

wherein $R_5$ and $R_6$ hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (-O-); wherein Z represents an oxa atom (-O-) or $C_jH_{2j}$, wherein $C_jH_{2j}$ is a valence bond or alkylene of one to 9 carbon atoms, inclusive, with one to 6 carbon atoms, inclusive, between $CR_5R_6-$ and the phenyl ring; wherein T is alkyl of one to 4 carbon atoms, inclusive, fluoro, chloro, trifluoromethyl, or $-OR_7-$, wherein $R_7$ is alkyl of one to 4 carbon atoms, inclusive, and s is zero or one; and wherein X is
(1) trans-CH=CH-,
(2) cis-CH=CH-,
(3) $-C\equiv C-$, or
(4) $-CH_2CH_2-$;

including the lower alkanoates thereof.

* * * * *